(12) United States Patent
Young et al.

(10) Patent No.: US 7,052,506 B2
(45) Date of Patent: May 30, 2006

(54) ULTRASONIC SURGICAL TOOL

(76) Inventors: Michael John Radley Young, Bremridge House, Bremridge, Ashburton, South Devon, TQ13 7JX (GB); Stephen Michael Radley Young, Bremridge House, Bremridge, Ashburton, South Devon, TQ13 7JX (GB)

(*) Notice: Subject to any disclaimer, the term of this patent is extended or adjusted under 35 U.S.C. 154(b) by 173 days.

(21) Appl. No.: 10/097,794

(22) Filed: Mar. 14, 2002

(65) Prior Publication Data

US 2002/0156491 A1 Oct. 24, 2002

Related U.S. Application Data

(63) Continuation of application No. PCT/GB00/03567, filed on Sep. 15, 2000.

(30) Foreign Application Priority Data

Sep. 17, 1999 (GB) .................................. 9921936

(51) Int. Cl.
*A61B 17/32* (2006.01)
(52) U.S. Cl. ....................... 606/169; 606/32
(58) Field of Classification Search ................ 606/32, 606/34, 37, 39, 40, 169; 600/437, 471
See application file for complete search history.

(56) References Cited

U.S. PATENT DOCUMENTS

| 5,322,055 | A | * | 6/1994 | Davison et al. .............. 606/169 |
| 5,456,683 | A |   | 10/1995 | Fritzsch et al. ................ 606/41 |
| 5,776,155 | A | * | 7/1998 | Beaupre et al. .............. 606/169 |
| 5,873,873 | A | * | 2/1999 | Smith et al. .................... 606/1 |
| 6,790,216 | B1 | * | 9/2004 | Ishikawa ..................... 606/169 |

FOREIGN PATENT DOCUMENTS

| DE | 42 38 619 A1 | 5/1994 |
| EP | 0 908 147 A1 | 4/1999 |
| WO | WO 99/35982 | 7/1999 |

OTHER PUBLICATIONS

Patent Abstracts of Japan, Publication No. 08275948 (Oct. 22, 1996), Olympus Optical Co. Ltd.

* cited by examiner

*Primary Examiner*—Julian W. Woo
(74) *Attorney, Agent, or Firm*—Heslin Rothenberg Farley & Mesiti P.C.

(57) ABSTRACT

The tool comprises an ultrasonic vibration generator and a waveguide operatively connected thereto at one end. The distal end of the waveguide is provided with cutting and/or coagulating means. A shroud is adapted to surround and isolate the waveguide, and an actuating rod surrounds the shroud, or vice versa. The shroud and actuating rod are detachably connected at their proximal ends to the generator.

14 Claims, 1 Drawing Sheet

ULTRASONIC SURGICAL TOOL

CROSS REFERENCE TO RELATED APPLICATION

This application is a continuation of international application PCT/GB00/03567 filed Sep. 15, 2000 and published under PCT Article 21(2) in English.

BACKGROUND OF THE INVENTION

The present invention relates to an ultrasonic surgical tool. More particularly, but not exclusively, it relates to a tool for use in a laparoscopic cutting/coagulating system, which is adapted to cut soft material such as flesh or blood vessels.

Such tools are known from our co-pending international application number PCT/GB99/00162. This application describes an apparatus adapted to utilize ultrasonic vibrations in a torsional mode, and this is preferred for the present invention. However, the present invention is not limited to torsional mode vibrations.

The above application describes an apparatus in which the ultrasonic vibrations are transmitted along an elongate waveguide to a distal end provided with cutting and/or coagulating means. A shroud surrounds the waveguide and is isolated from the vibration thereof. The cutting and/or coagulating means comprises a torsionally vibratable element connected to the waveguide in combination with a static non-vibratable element connected to the shroud. This static element may be brought into and out of engagement with the vibratable element by means of an actuating rod extending concentrically within or as part of the shroud. The actuating rod is connected at its proximal end to a scissors grip or other type of operating mechanism.

One disadvantage of such systems lies in the fact that, at the distal end of the apparatus, it comprises a waveguide, surrounded coaxially by an actuating rod which in turn is surrounded coaxially by the shroud. When operating on a patient, bodily fluids at positive pressures may find their way into these concentric spaces, as may some body solids. It is then very difficult to clean the apparatus. It would be advantageous if it were to be possible to detach and discard the shroud and actuating rod, to be replaced by a fresh combination.

BRIEF SUMMARY OF THE INVENTION

It is an object of the present invention to provide an ultrasonic surgical tool which is provided with a disposable shroud system which can be easily and quickly detached from the apparatus and replaced quickly and easily by a replacement shroud.

According to a first aspect of the present invention, there is provided a surgical tool comprising means to generate ultrasonic vibrations, a waveguide operatively connected at a proximal end to said generating means and extending to a distal end provided with cutting and/or coagulating means, shroud means adapted to surround and isolate said waveguide, and actuating rod means coextensive with said shroud means, said shroud means and said actuating rod means being detachably connected at their proximal ends to said generating means.

Preferably, said generating means comprises a conversion horn and at least one axial mode driver mounted substantially tangentially thereto, whereby torsional mode vibrations are produced.

The cutting and/or coagulating means may comprise a torsionally vibratable element connected to said waveguide in combination with a static non-vibratable element which is so mounted to said shroud means that it is isolated from said ultrasonic vibrations.

The actuating rod means may be so connected at its distal end to said static element as to cause pivotal movement thereof into and out of engagement with said vibratable element.

The actuating rod means may be detachably connected at its proximal end to manually operable means, optionally a pair of scissors type grips connected by rack and pinion means to said actuating rod means.

The actuating rod means preferably comprises a tubular member surrounding said waveguide.

The shroud means may also comprise a tubular member and in this case, one of the tubular members may be polygonal in cross-section and be adapted to contact an inner surface of the other tubular member, which is substantially cylindrical, only at apices of said polygon.

The shroud means and actuating rod means may be detachably connected together to said generating means by a connector means.

This connector means may be a nut and may also comprise a projecting detent resiliently deformable out of engagement to allow separation.

According to a second aspect of the present invention, there is provided a shroud means including actuating rod means for detachable connection to a surgical tool including a waveguide operatively connected at a proximal end to means to generate ultrasonic vibrations.

BRIEF DESCRIPTION OF THE DRAWING

An embodiment of the present invention will now be more particularly described by way of example and with reference to the accompany drawing, in which.

DETAILED DESCRIPTION

Figure 1:
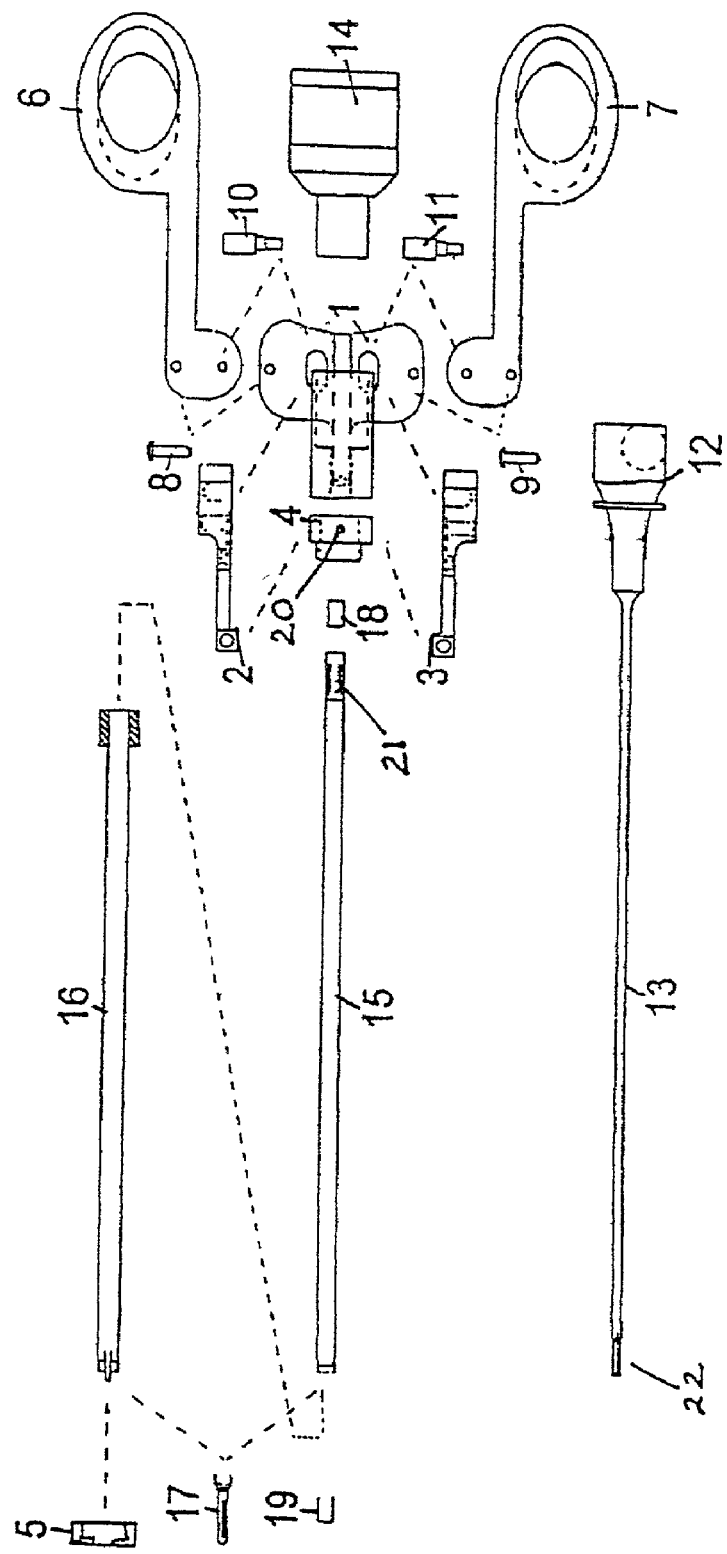
FIG. 1 shows a tool embodying the present invention in separated condition.

Referring now to the drawing, the ultrasonic surgical tool comprises a handle section, including a chassis 1, right 2 and left 3 connecting rods, which are attached respectively to right 6 and left 7 handlebows. The configuration of these bows is not critical and other variations are possible, such as are described in our co-pending UK patent application number 9906701.9. The bows 6 and 7 are connected to the chassis 1 by means of respective pivot pins 8 and 9 and connecting rod drive pins 10 and 11.

An ultrasonic piezo electric ceramic transducer 14 is mounted tangentially to a conversion horn 12 to form a generator of ultrasonic vibrations in torsional mode. Such vibrations are transmitted to waveguide 13 which has at its distal end a vibratable part of the cutting and/or coagulating means 22. The generator 12, 14 is mounted to the chassis 1.

An outer shroud 16 acting as an actuating rod is adapted to surround an inner shroud 15, the pair being isolated from the waveguide 13 by PTFE bushes 18 and 19 at proximal and distal ends of the combined shroud. Both shrouds are preferably thin walled tubes of stainless steel, although other materials may be used. The shrouds 15, 16 are connected to the chassis via the inner tubular member 15 of the shroud which may be connected to a quick release mechanism 4 which is itself attached to chassis 1. A flexible protruding tongue 21 of the inner shroud 15 is biased to spring outwardly so that, once the tube has been inserted into the quick release member 4, it will maintain the inner shroud 15 locked in position. When button 20 on the member 4 is depressed, the tongue 21 becomes disengaged which enables the inner shroud 15 to be detached from the release member 4. In order to prevent accidental disengagement, a nut 5 engages around the outer shroud 16 to hold both that and the inner shroud 15 in engagement with the quick release member 4.

A hinged jaw 17 is attached to be supported by the inner shroud 15 and actuated by movement of the outer shroud 16, or alternatively to be supported by the outer shroud 16 and actuated by movement of the inner shroud 15.

In use, once the concentric spaces between the waveguide 13 and inner 15 and outer 16 shroud members have become clogged with body fluids or solids, the assembly of inner 15 and outer 16 shroud members and jaw 17 may be removed from the handle and generator by unscrewing the nut 5 and depressing the button 20. They may then be discarded.

What is claimed is:

1. A surgical tool comprising means to generate ultrasonic vibrations, a waveguide operatively connected at a proximal end to said generating means and extending to a distal end provided with cutting and/or coagulating means, shroud means adapted to surround and isolate said waveguide, actuating rod means extending coextensively with said shroud means and manually operable means to control said actuating rod means, wherein said shroud means and said actuating rod means are detachably connectable at their proximal ends to said generating means and to said manually operable means, whereby said shroud means and said actuating rod means are detachable from said generating means and said manually operable means without disconnecting said waveguide from said generating means.

2. A surgical tool as claimed in claim 1, wherein the shroud means and the actuating rod means are together detachably connected to said generating means and said manually operable means by connector means.

3. A surgical tool as claimed in claim 2, wherein the connector means comprises a nut and a projecting detent resiliently deformable out of engagement to allow separation.

4. A surgical tool as claimed in claim 1, wherein the manually operable means comprises a pair of scissors type grips and rack and pinion means and is detachably connected to said actuating rod means.

5. A surgical tool as claimed in claim 1, wherein the cutting and/or coagulating means comprises an ultrasonically vibratable element connected to said waveguide in combination with a non-vibratable static element which is so mounted to said shroud means that it is generally isolated from said ultrasonic vibrations, and wherein the actuating rod means is so connected at its distal end to said non-vibratable static element as to cause pivotal movement thereof into and out of engagement with said vibratable element.

6. A surgical tool as claimed in claim 5, wherein the cutting and/or coagulating means comprises hemostatic cutting means.

7. A surgical tool as claimed in claim 1, wherein the actuating rod means comprises a tubular actuating rod member surrounding said waveguide.

8. A surgical tool as claimed in claim 7, wherein the shroud means comprises a shroud tubular member surrounding said actuating rod means.

9. A surgical tool as claimed in claim 8, wherein the tubular actuating rod member is polygonal in cross-section and is adapted to contact an inner surface of the shroud tubular member, which is substantially cylindrical, only at apices of said polygon.

10. A surgical tool as claimed in claim 1, wherein the shroud means comprises a tubular member surrounding said waveguide.

11. A surgical tool comprising means to generate ultrasonic vibrations, a waveguide operatively connected at a proximal end to said generating means and extending to a distal end provided with cutting and/or coagulating means, shroud means adapted to surround and isolate said waveguide, actuating rod means extending coextensively with said shroud means and manually operable means to control said actuating rod means, wherein said shroud means and said actuating rod means are detachably connectable at their proximal ends to said generating means and to said manually operable means, wherein the shroud means comprises a tubular shroud member surrounding said waveguide, and wherein the actuating rod means comprises an actuating rod tubular member surrounding said shroud means.

12. A surgical tool as claimed in claim 11, wherein the tubular shroud member is polygonal in cross-section and is adapted to contact an inner surface of the actuating rod tubular member, which is substantially cylindrical, only at apices of said polygon.

13. A surgical tool comprising means to generate ultrasonic vibrations, a waveguide operatively connected at a proximal end to said generating means and extending to a distal end provided with cutting and/or coagulating means, shroud means adapted to surround and isolate said waveguide, actuating rod means extending coextensively with said shroud means and manually operable means to control said actuating rod means, wherein said shroud means and said actuating rod means are detachably connectable at their proximal ends to said generating means and to said manually operable means, wherein said generating means comprises a conversion horn and at least one axial mode driver mounted substantially tangentially thereto, whereby torsional mode vibrations are produced.

14. A shroud means and an actuating rod means coextensive therewith detachably connected to a surgical tool, which tool includes a waveguide operatively connected at a proximal end to means to generate ultrasonic vibrations, and to manually operable means adapted to control said actuating rod means, wherein said shroud means and said actuating rod means are detachable from said tool and from said manually operable means without disconnecting the waveguide from the means to generate ultrasonic vibrations.

* * * * *